US008845750B2

(12) United States Patent
Slavitt

(10) Patent No.: US 8,845,750 B2
(45) Date of Patent: Sep. 30, 2014

(54) JOINT RESURFACING PROSTHETIC IMPLANT SYSTEM

(76) Inventor: Jerome A. Slavitt, Pikesville, MD (US)

(*) Notice: Subject to any disclaimer, the term of this patent is extended or adjusted under 35 U.S.C. 154(b) by 156 days.

(21) Appl. No.: 13/472,918

(22) Filed: May 16, 2012

(65) Prior Publication Data

US 2012/0296439 A1    Nov. 22, 2012

Related U.S. Application Data

(60) Provisional application No. 61/486,385, filed on May 16, 2011.

(51) Int. Cl.
*A61F 2/30* (2006.01)
*A61F 2/42* (2006.01)
*A61B 17/16* (2006.01)

(52) U.S. Cl.
CPC ..... *A61F 2/4225* (2013.01); A61F 2002/30841 (2013.01); *A61F 2/4241* (2013.01); A61F 2002/30574 (2013.01); A61F 2002/30878 (2013.01); A61F 2002/30848 (2013.01); *A61B 17/1604* (2013.01); A61F 2002/30904 (2013.01); A61F 2002/30299 (2013.01); A61F 2002/30253 (2013.01); A61F 2002/30151 (2013.01)
USPC .......... 623/23.43; 623/21.19; 623/21.15; 623/21.12; 623/19.13; 623/18.11

(58) Field of Classification Search
CPC .............. A61F 2002/4228; A61F 2002/423; A61F 2002/4233; A61F 2002/4235; A61F 2002/4238; A61F 2/4241; A61F 2002/4243; A61F 2002/4246; A61F 2002/4248; A61F 2002/4251; A61F 2002/4258
USPC .......... 623/18.11, 19.11, 19.13, 20.32, 21.11, 623/21.12–22.19, 23.39, 23.43
See application file for complete search history.

(56) References Cited

U.S. PATENT DOCUMENTS

| | | | |
|---|---|---|---|
| 4,030,143 | A | 6/1977 | Elloy et al. |
| 4,106,130 | A | 8/1978 | Scales |
| 4,156,296 | A | 5/1979 | Johnson et al. |
| D285,968 | S | 9/1986 | Kinnett |

(Continued)

OTHER PUBLICATIONS

Townley, Charles O. "Metalic Hemiarthroplasty Resurfacing Prosthesis." Biologically Oriented Prostheses Biopro. Brochure No. 17541. Date unavailable.

(Continued)

*Primary Examiner* — David Isabella
*Assistant Examiner* — Suba Ganesan
(74) *Attorney, Agent, or Firm* — Whiteford, Taylor & Preston, LLP; Gregory M. Stone

(57) ABSTRACT

A joint resurfacing prosthetic implant system is disclosed having an anatomically-shaped implant to replace a joint at a pedal digit or finger, including a head having an elliptical bearing surface disposed for engaging the end of an adjacent bone and a seating surface opposite the bearing surface, an elongated stem extending distally from the seating surface, and a flange on the circumference of the device and extending distally from the seating surface. The flange includes one or more portals and a removed section configured to avoid impinging upon a tendon during and after implantation of the prosthetic. A specialized tool is also provided to facilitate the resection of the bone for implantation. The specialized tool includes an elliptical template having a cutting edge and a center insert that is sized and configured to match a reamer used to bore into the bone for insertion of the implant.

16 Claims, 9 Drawing Sheets

(56) References Cited

U.S. PATENT DOCUMENTS

| | | |
|---|---|---|
| 4,642,122 A | 2/1987 | Steffee |
| 4,731,087 A | 3/1988 | Sculco et al. |
| 4,908,031 A | 3/1990 | Frisch |
| 5,037,440 A | 8/1991 | Koenig |
| 5,326,366 A * | 7/1994 | Pascarella et al. ......... 623/21.19 |
| 5,405,401 A | 4/1995 | Lippincott, III et al. |
| 5,458,648 A | 10/1995 | Berman et al. |
| 5,601,567 A | 2/1997 | Swajger et al. |
| 5,725,585 A | 3/1998 | Zobel |
| 5,776,203 A | 7/1998 | Spalding et al. |
| 6,096,084 A | 8/2000 | Townley |
| 6,159,216 A | 12/2000 | Burkinshaw et al. |
| 6,309,419 B1 | 10/2001 | de Juan, Jr. et al. |
| 6,319,284 B1 | 11/2001 | Rushdy et al. |
| 6,379,386 B1 | 4/2002 | Resch et al. |
| 6,673,115 B2 | 1/2004 | Resch et al. |
| 6,682,565 B1 | 1/2004 | Krishnan |
| 6,699,292 B2 | 3/2004 | Ogilvie et al. |
| 7,175,667 B2 | 2/2007 | Saunders et al. |
| 2007/0078518 A1 | 4/2007 | Lavi |
| 2007/0282451 A1 | 12/2007 | Metzger et al. |
| 2008/0195215 A1* | 8/2008 | Morton ..................... 623/18.11 |
| 2008/0221697 A1 | 9/2008 | Graser |

OTHER PUBLICATIONS

Giza, Eric, et al. "First metatarsophalangeal hemiarthoplasy for hallux rigidus." Int Orthop. Dec. 2010. vol. 31, No. 8. pp. 1193-11983. Retrieved from http://www.ncbi.nlm.nih.gov/pmc/articles/PMC2989092/ on Feb. 27, 2014.

* cited by examiner

SECTION C-C

JOINT RESURFACING PROSTHETIC IMPLANT SYSTEM

CROSS REFERENCE TO RELATED APPLICATION

This application is based upon and claims priority from U.S. Provisional Patent Application Ser. No. 61/486,385 entitled "Implantable Joint Resurfacing Prosthetic," filed with the U.S. Patent and Trademark Office on May 16, 2011 by the inventor herein, the specification of which is incorporated herein by reference.

FIELD OF THE INVENTION

This invention relates in general to a prosthetic implant, and, more particularly, to a prosthetic implant system that resurfaces a bone, especially in the foot.

BACKGROUND OF THE INVENTION

The medical profession for many years has used prosthetic devices as joint surfaces to replace defective natural joints. Typically, such devices consist of one or two prosthetic members that are implanted into or attached to the anatomy of the subject at the location of the defective joint. In particular, various types of prosthetic joints have been developed to replace diseased or damaged human toe joints. Toe joint prostheses are known in the art and commonly comprise one or two components: a) having opposed ball and socket parts, and b) individual head or base parts. Examples of prosthetic bone joint devices can be found in U.S. Pat. Nos. 4,106,130; 4,156,296; 4,908,031; 5,326,366; 5,725,585; 5,037,440; and 7,175,667.

Metal prosthetic implant devices, typically made of cobalt chrome, titanium or a titanium alloy, eliminate the health concerns of using silicone devices. When using metal prosthetic implants, either one or both sides of the joint are fitted with a metal implant. However, over a period of time, the bone continues to grow and can overlap the surface of the prosthetic device causing reduced functionality of the joint, which may ultimately require additional surgical procedures. Additionally, these prosthesis components can become loose with time (known as subluxation) and can cause problems with one surface of one of the prosthetic components sliding over a surface of the other prosthetic component that is not properly oriented relative to the one component, or in the case of a partial prosthetic component, malalignment of the opposing joint surface. All of these and other aspects of prior art prosthetic bone joint devices may limit their viability, in some cases ultimately requiring costly additional surgical procedures that can cause the patient unnecessary pain and risk of complications. Thus, there remains a need in the art for a prosthetic implant, and a system for its implantation, that significantly reduces shifting after its implantation, can maintain the same orientation with respect to the joint it is intended to repair, and has improved, long-term viability over previously known prosthetic implants by eliminating bone overgrowth onto the implant, thereby significantly increasing the lifetime of the implant and joint function.

SUMMARY OF THE INVENTION

Briefly summarized, disclosed herein is an improved prosthetic implant system adapted for replacement of a human toe joint, which includes at least one one-piece prosthetic implant member for implantation into the bone of the joint.

It is, therefore, an object of an embodiment of the invention to provide a joint resurfacing prosthetic device that avoids the disadvantages of the prior art.

It is another object of an embodiment of the invention to provide a joint resurfacing prosthetic implant system for replacing a joint surface for a bone in the foot or the hand.

It is yet another object of an embodiment of the invention to provide a joint resurfacing prosthetic implant system that is economical to produce and uncomplicated in configuration. A related object is to provide a joint resurfacing prosthetic implant system configured to avoid impinging on a tendon.

Still yet another object of an embodiment of the invention is to provide a joint resurfacing prosthetic implant system that fits over the end of a damaged bone. A related object is to provide a tool for preparing a bone to receive a joint resurfacing prosthetic. A still further related object is to provide a joint resurfacing prosthetic having portals to view the fit of the prosthetic onto a bone.

In accordance with the above objects, an implantable joint resurfacing prosthetic implant system is disclosed having an anatomically-shaped implant configured to replace a joint at a specified pedal digit or finger. A joint resurfacing prosthetic is provided including a head having an elliptical bearing surface disposed for engaging the end of an adjacent bone, and a generally planar seating surface opposite the bearing surface. An elongated stem extends distally from the seating surface and includes a plurality of serrations along the edge of the stem for anchoring the stem within a prepared bone. The head further includes a flange disposed on or adjacent the circumference of the device and extending distally from the seating surface. The flange includes one or more portals and a removed section.

A specialized tool is provided to facilitate the resection of the bone for implantation. The appropriate bone is prepared for implantation of the base member of the prosthesis by resecting the end of the bone proximate to the joint being replaced. The bone is resected to present a flat surface at the end of the bone that is perpendicular to the longitudinal axis of the bone. The specialized tool includes an appropriately sized elliptical template having a cutting edge. The elliptical template is chosen that most closely approximates the cross sectional area of the flat surface of the resected bone. The tool includes a center insert that is sized and configured to match a reamer used to bore into the bone for insertion of the implant.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF A PREFERRED EMBODIMENT

The invention summarized above may be better understood by referring to the following description, which should be read in conjunction with the accompanying drawings in which like reference numbers are used for like parts. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
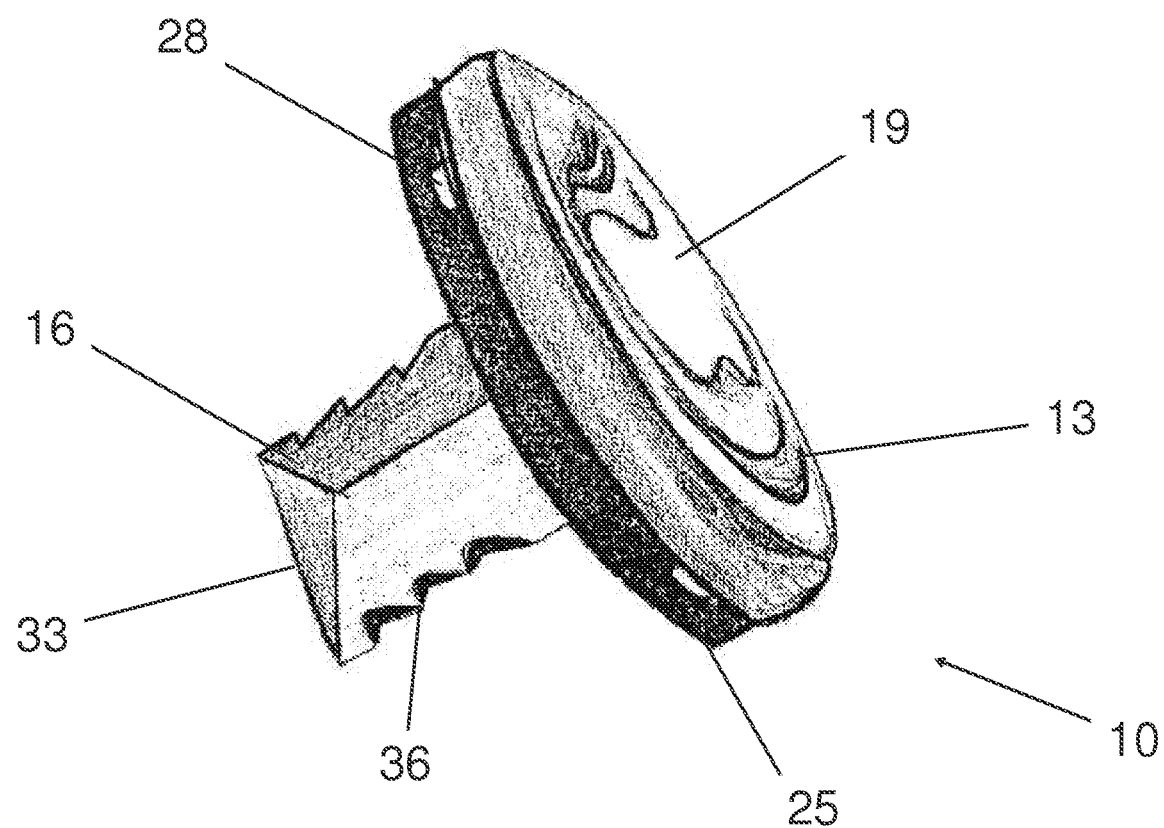
FIG. 1 shows a perspective view of a joint resurfacing prosthetic according to certain aspects of an embodiment of the invention.

Referring to the drawings, FIG. 1 shows an implant, indicated generally as 10, according to certain aspects of a particularly preferred embodiment of the invention. Implant 10 comprises a head 13 and an elongated stem 16. The head 13 comprises an elliptically shaped bearing surface 19 disposed for engaging the end of an adjacent bone and a generally planar seating surface 22 opposite the bearing surface 19. The bearing surface 19 may be slightly concave. In a preferred embodiment, the implant 10 is sized according to the patient and may be provided in a number of standard incremental sizes. For example, in some embodiments, the A dimension for implant 10, shown in FIG. 4, may range from approximately 0.67 inches to approximately 0.91 inches, and the B dimension for implant 10, shown in FIG. 4, may range from approximately 0.51 inches to approximately 0.69 inches.

The head 13 further includes a flange 25 disposed on the circumference of the implant 10 and extending distally from the seating surface 22. Flange 25 is sized and configured to fit like a cap over the end of a prepare bone. Flange 25 defines a peripheral sidewall extending distally from head 13 and extending along or adjacent to the circumferential edge of head 13. Flange 25 may be added to joined to head 13 using any of a variety of metal-to-metal joining techniques as are known in the art, or may alternatively be formed integrally with head 13.

Figure 2:
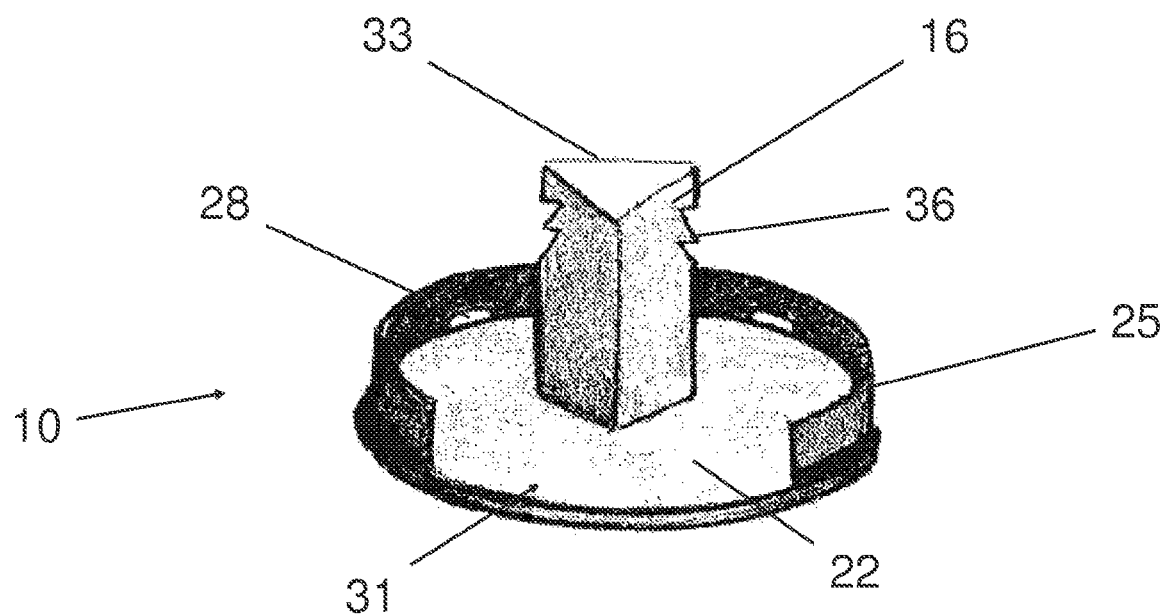
FIG. 2 shows a bottom perspective view of a joint resurfacing prosthetic according to certain aspects of an embodiment of the invention.

Flange 25 includes one or more portals 28 extending through the peripheral sidewall defined by flange 25. Portals 28 may be immediately adjacent upper surface of head 13, or alternatively may be positioned slightly away from upper surface of head 13 and along the periphery of flange 25. Flange 25 also comprises an open area 31, such that the peripheral sidewall defined by flange 25 is not a continuous wall throughout its length around the circumference of head 13. More particularly, open area 31, as shown in FIG. 2, is appropriately sized and configured to avoid impingement on the tendon associated with the joint under repair. Open area 31 need not extend through the entire height of the sidewall defined by flange 25, it only being important that open area 31 be open at the distal edge of such sidewall (i.e., the edge opposite the edge of flange 25 that attaches to head 13).

Figure 3:
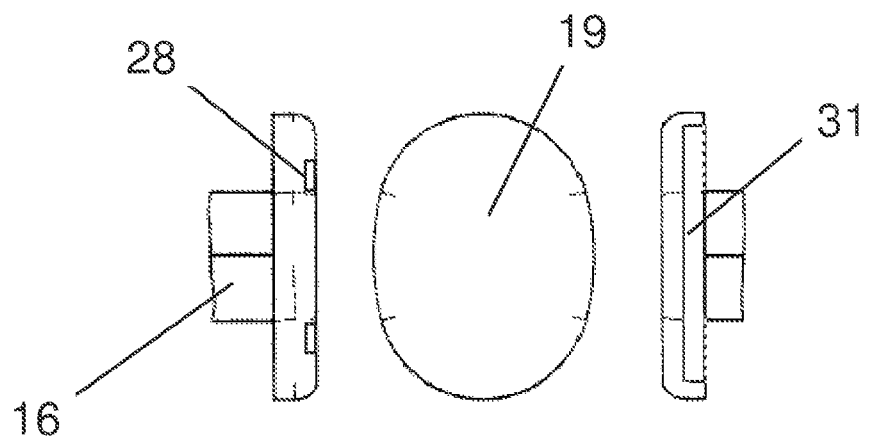
FIG. 3 shows top and side views of the bearing surface for a joint resurfacing prosthetic according to certain aspects of an embodiment of the invention.
Figure 6:
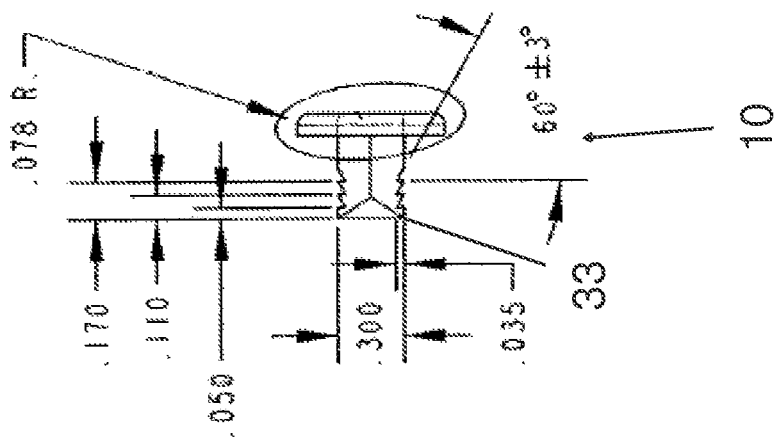
FIG. 6 is a side view of the joint resurfacing prosthetic of FIG. 4.
Figure 5:
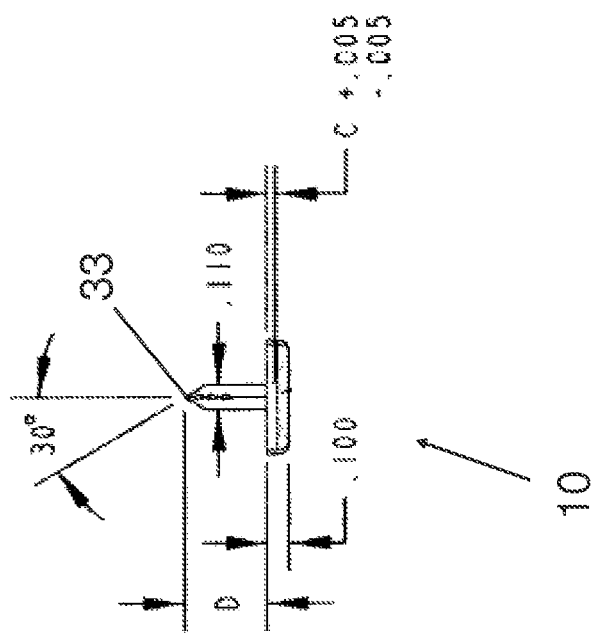
FIG. 5 is a side view of the joint resurfacing prosthetic of FIG. 4.

Implant 10 may have a top and bottom orientation that can be determined by the location of the one or more portals 28 on the bottom and the open area 31 on the top, as shown in FIG. 3. The thickness of the head 13 and the width of the flange 25 are also sized according to the patient. The dimensions shown in FIGS. 4, 5, and 6 are approximate, and other sizes can be used without departing from the spirit and scope of the invention.

The elongated stem 16 provides the mechanism whereby the implant 10 is attached to the bone. The stem 16 extends perpendicularly from the seating surface 22 and may, in a preferred embodiment, be machined from the same metal solid as the head 13. Alternatively, the stem 16 may be attached to the head 13 with any number of rigid metal-to-metal attachment methods known in the art. The stem 16 is sized according to the patient and may be provided in a number of standard incremental sizes. For example, in some embodiments, the length D dimension for implant 10, shown in FIG. 5, may range from approximately 0.37 inches to approximately 0.5 inches. The width dimension of stem 16 is generally related to the overall size of implant 10 and may vary according to the same.

Figure 4:
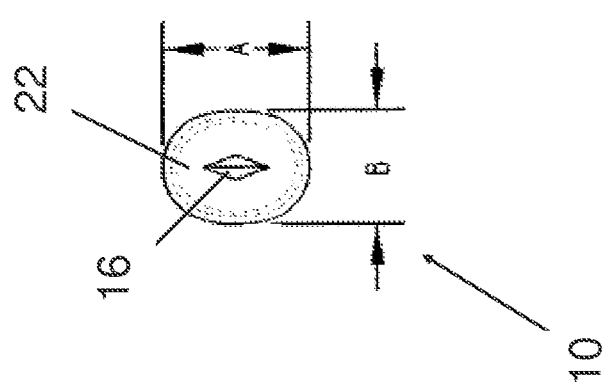
FIG. 4 shows a bottom plan view of a joint resurfacing prosthetic according to certain aspects of an embodiment of the invention.
Figure 4A:
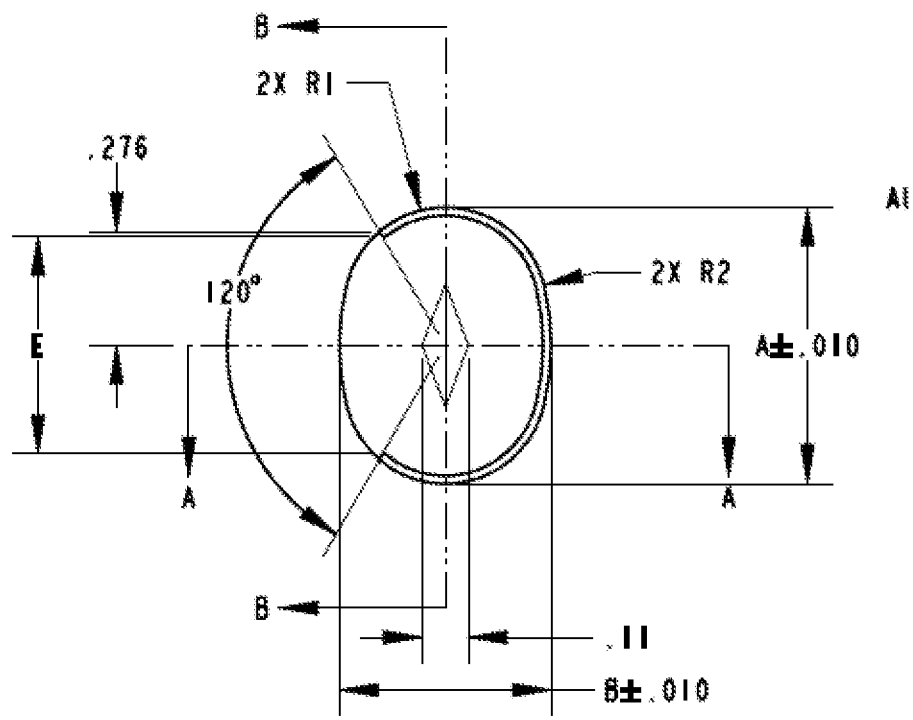
FIG. 4(a) shows a close-up bottom plan view of the a joint resurfacing prosthetic of FIG. 4.
Figure 4B:
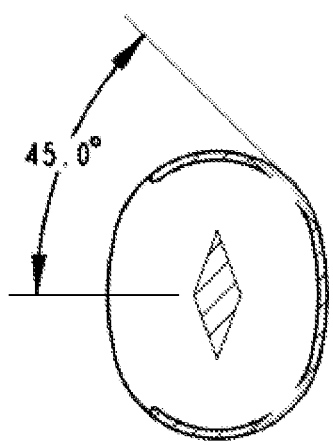
FIG. 4(b) shows a close-up, bottom cross-sectional view of the resurfacing prosthetic of FIG. 4 along section line C-C.
Figure 5A:
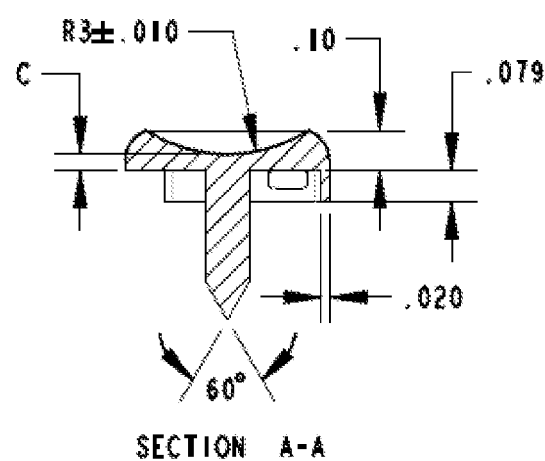
FIG. 5(a) is a close-up, side cross-sectional view of the resurfacing prosthetic of FIG. 4 along section line A-A of FIG. 4A.
Figure 6A:
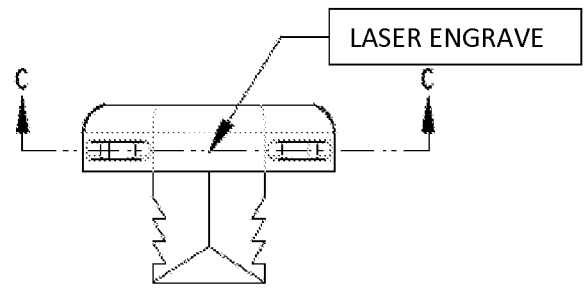
FIG. 6(a) is a close-up side plan view of the joint resurfacing prosthetic of FIG. 4.
Figure 6B:
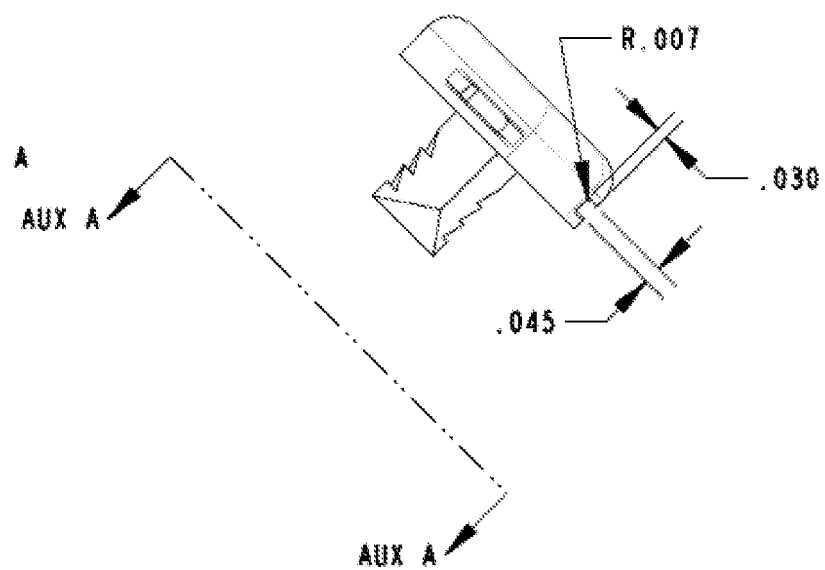
FIG. 6(b) is a close-up, side perspective view of the joint resurfacing prosthetic of FIG. 4.
Figure 6C:
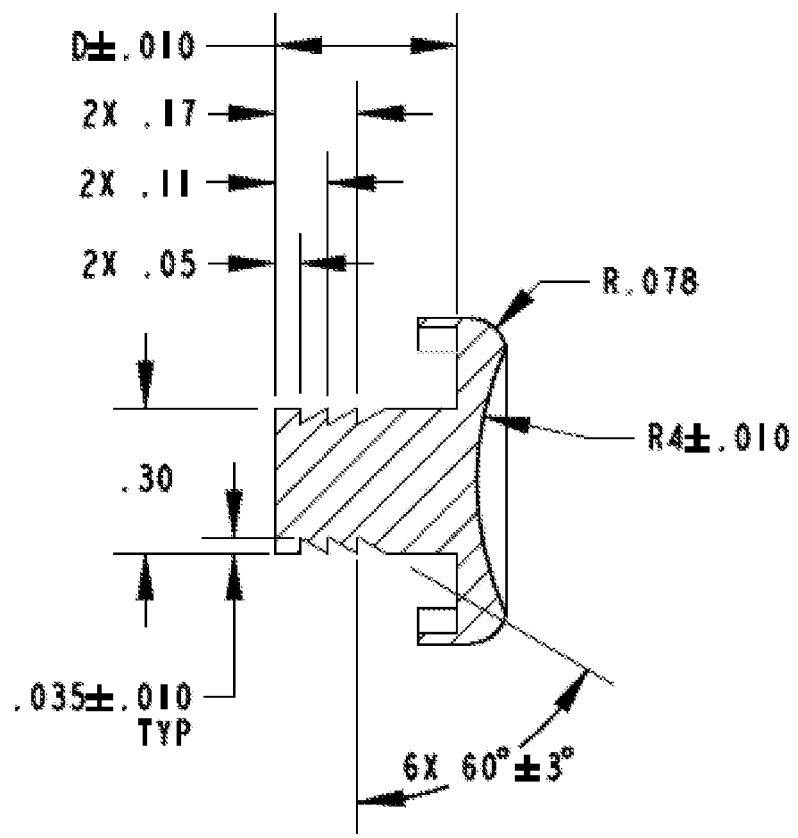
FIG. 6(c) is a close-up, side cross-sectional view of the resurfacing prosthetic of FIG. 4 along section line B-B of FIG. 4(a).

Stem 16 generally comprises a wedge having a diamond-shaped cross section, as shown in FIG. 4. The stem 16 terminates in a wide tip 33 such as shown in FIGS. 5 and 6. On each of the acute angle edges of the stem 16, a plurality of serrations 36 is provided to facilitate the adherence of the stem 16 within the bone, especially after post-operative bone growth. The serrations 36 provide adherence within the bone, especially over time as bone growth extends into the indentation around the serrations 36 and firmly retains the implant 10 in place. The serrations 36, as shown in FIGS. 1 and 2, may be as much as 20%-30% of the width dimension of the stem 16.

Figure 7:
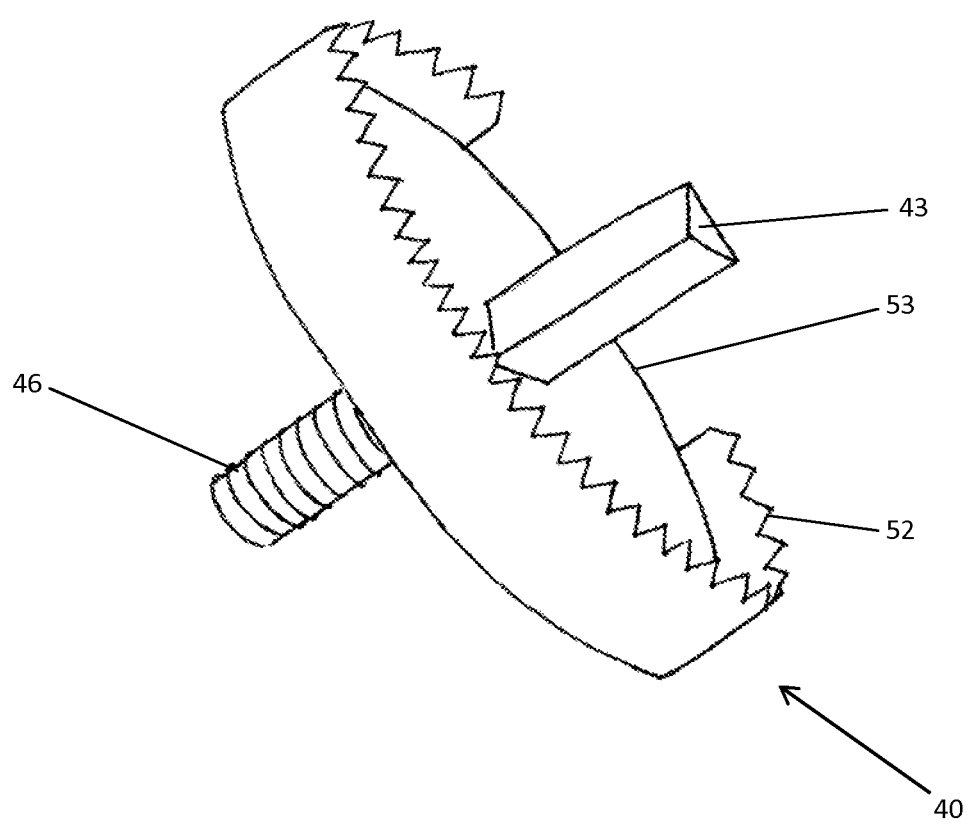
FIG. 7 shows a perspective view of an implant punch for use with a joint resurfacing prosthetic according to certain aspects of an embodiment of the invention.

Referring to FIG. 7, a specialized implant punch, indicated generally as 40, is provided. In a preferred embodiment, the implant punch 40 has elements matching the dimensions of the implant 10 to be used; that is, the implant punch 40 may come in a variety of sizes to match the variety of sizes of the implant 10. A surgical implant kit will preferably include sizers, reamers, and instrument handles that are well known in the art. On one side, the implant punch 40 has a center insert 43 that is sized and configured to match a reamer used to create a cavity for insertion of the stem 16 of the implant 10 into a prepared bone. This enables the punch 40 to follow the same pathway obtained from the reamer. On the opposite side, the implant punch has a threaded post 46 for attachment to a handle. The punch 40 also includes a cutting edge that is serrated on its entire cutting surface 52. Cutting surface 52 is preferably sized so as to mark the portion of bone that should be cut away in order to receive flange 25 in an appropriately close fit. Cutting surface 52 also preferably has an open section 53 that generally corresponds in size and position with open area 31 on flange 25.

In preparation for the implantation of the prosthetic joint, the end of the bone of the joint to be replaced is resected to dimensions that provide a close fit between the component of the prosthetic joint and the resected end of the bone. A groove or hole can be cut into the resected end of the bone, to receive the above-discussed stem 16 of the implant 10. The implant 10 for the prosthetic joint is implanted in a proper position on the resected end of the bone. This is done by inserting the stem 16 into a cut made in the ends of the bone and, if necessary, cementing the implant 10 in place.

Figure 8:
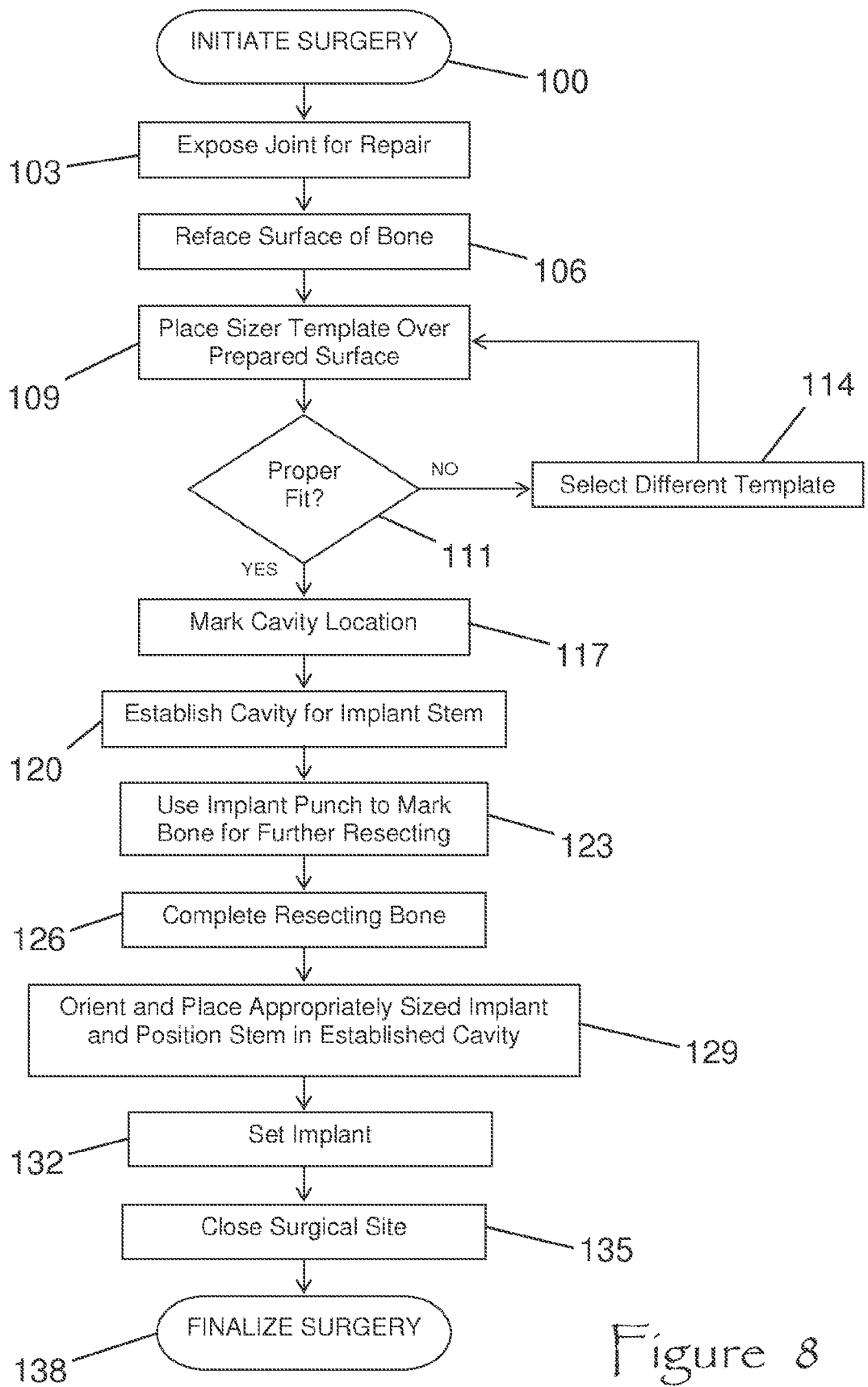
FIG. 8 is a flowchart of method steps associated with surgically placing a joint resurfacing prosthetic in accordance with certain aspects of an embodiment of the invention.

Prior to implantation of the prosthesis of the present invention, the bone of the joint to be replaced must be properly resected to accommodate the implantation of the implant 10. Below is a brief description of the methodology associated with the selection and placement of an appropriately sized implant 10. It is recognized that the steps described herein are general in nature and do not include many of the individual specific surgical procedure steps that would be required for the type of prosthetic placement associated with a hemiarthroplasty resurfacing procedure. These steps, however, do disclose those aspects of the method that allow a physician to improve the placement of the implant 10. Referring to FIG. 8, the surgery is initiated at Step 100, with the process of exposing the joint at Step 103. An incision is made through the skin and the superficial fascia layer and retracted both medially and laterally. An appropriate portion of the proximal surface of the bone is resected at Step 106. Typically, using a power saw, a section is cut in a common flat plane transversely through the base of the proximal bone from dorsal to plantar The width of the base transected should at a minimum correspond to the thickness of the implant head 13. The physician should be careful not to resect too much bone. The physician may then utilize a well-known sizer tool by placing the tool over the prepared face and selecting the most appropriate template size to match the prepared face at Step 109. The implant 10 is sized using a sizing instrument. Indicia provided on the template elements in the tool provide the physician with the appropriate implant device size to be utilized. The sizing instrument edges should extend just past the bone margins.

If the selected template size is not the proper fit as determined at Step 111 the physician selects a new size of template at Step 114 and again places the sizer tool over the prepared face at Step 109. If at Step 111 a proper template fit is identified, then the physician proceeds at Step 117 to orient and align the template and thereafter mark the cavity location for the stem 16 of the implant 10. This location is determined by appropriate marking of the surface of the bone (as resected) as is known in the art. A temporary hole is made with a punch tool, through a hole in the sizing instrument. The physician then removes the sizing tool from the surgical site and selects the proper sized implant 10 and implant punch 40 that matches the indicia on the selected template tool.

At Step 120, a cavity is established for the stem 16 of the implant 10 utilizing a reamer tool directed into the marked location on the proximal surface of the bone. Once the cavity is established, the physician, at Step 123, then uses the implant punch 40 to mark the end of the bone for further reshaping.

At Step 126, the physician completes resecting the bone by cutting sufficient bone to enable the flange 25 of the implant 10 to fit over the end of the prepared bone.

Once the appropriate size is determined and the head of the bone is remodeled, the implant 10 is fitted into place. The physician orients and places the stem 16 of the implant 10 within the established cavity at Step 129. The properly sized implant 10 is then inserted and completely seated. At Step 132, an impact tool is implemented to set the implant 10 in place until the implant 10 is flush with the bone. The physician can verify that the implant 10 is flush with the bone by viewing the position of the implant 10 with respect to the bone through the one or more portals 28 provided in the flange 25 of the implant 10. The surgical site is closed at Step 135 and the surgery is finalized at Step 138 in a manner well known in the art.

It will be appreciated by persons skilled in the art that numerous variations and/or modifications may be made to the invention as shown in the specific embodiments without departing from the spirit or scope of the invention as broadly described. Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention might be practiced otherwise than as specifically set forth herein. The present embodiments are, therefore, to be considered in all respects as illustrative and not restrictive.

I claim:

1. A prosthetic implant system comprising:
a joint resurfacing prosthetic comprising
an elliptical head having an upper surface and a planar lower surface, and an outer edge extending around a circumference of the upper and planar lower surfaces, said elliptical head having a major ellipse axis and a minor ellipse axis;
a flange extending distally from said planar lower surface, said flange having a proximal edge affixed to said planar lower surface and a distal edge opposite said proximal edge and having a uniform width from said proximal edge to said distal edge throughout a full length of said flange, said flange defining an exterior, circumferential sidewall of said elliptical head extending circumferentially around said planar lower surface of said elliptical head from a first end on a first side of said minor ellipse axis and terminating at a second end on a second side of said minor ellipse axis opposite said first side, such that an open portion extends along said planar lower surface between said first end and said second end, and said flange having at least one portal extending through said sidewall, wherein said portal is positioned along said sidewall to allow viewing through said portal of contact between said planar lower surface of said elliptical head and a bone in which said prosthetic is implanted after said prosthetic is fully seated in said bone; and
an elongated stem extending distally from said planar lower surface of said head.

2. The prosthetic implant system of claim 1, wherein said upper surface of said elliptical head comprises a slightly concave surface.

3. The prosthetic implant system of claim 2, wherein said upper surface is configured to engage an end of a bone adjacent to a bone in which said joint resurfacing prosthetic is implanted.

4. The prosthetic implant system of claim 1, wherein said lower planar surface comprises a generally planar seating surface configured for facing contact across said generally planar seating surface against a bone in which said prosthetic is implanted.

5. The prosthetic implant system of claim 4, wherein at least one portal is positioned on a first side of said minor ellipse axis, and said flange having a second portal positioned on a second side of said minor ellipse axis.

6. The prosthetic implant system of claim 5, wherein each said portal has a proximal edge that is aligned with the planar lower surface.

7. The prosthetic implant system of claim 1, wherein said open portion of said flange extends for less than half of the circumference of said flange.

8. The prosthetic implant system of claim 1, wherein said open portion extends towards said planar lower surface of said elliptical head from said distal edge of said flange.

9. The prosthetic implant system of claim 1, wherein said open portion is sized to unimpinge a tendon extending between a first bone in which said joint resurfacing prosthetic is implanted and a second bone adjacent said first bone.

10. The prosthetic implant system of claim 1, said elongated stem having a plurality of serrations along an outer edge of said stem.

11. The prosthetic implant system of claim 1, said elongated stem having a wedge-shaped tip at a distal end of said stem.

12. The prosthetic implant system of claim 1, further comprising:

an implant punch configured for preparing a bone to receive said joint resurfacing prosthetic.

13. The prosthetic implant system of claim 12, said implant punch further comprising:
a punch top surface and a punch bottom surface;
a connecting post extending outward from said punch top surface and configured for attachment to a handle;
a center insert extending outward from said bottom surface; and
a cutting edge extending outward from said bottom surface.

14. The prosthetic implant system of claim 13, wherein said cutting edge has an open portion along a circumference of said cutting edge.

15. The prosthetic implant system of claim 13, wherein said cutting edge extends circumferentially around at least a portion of said punch bottom surface.

16. The prosthetic implant system of claim 13, wherein said center insert is sized to fit within a cavity that has been prepared in a bone into which said joint resurfacing prosthetic is to be implanted, wherein said cavity is sized to receive said stem of said joint resurfacing prosthetic.

* * * * *